United States Patent [19]
McCarthy et al.

[11] Patent Number: 5,616,758
[45] Date of Patent: Apr. 1, 1997

[54] CATIONIC SILICONES

[75] Inventors: James P. McCarthy, Janesville, Wis.;
George H. Greene, Morristown, N.J.;
Anthony G. DeWar, Janesville, Wis.

[73] Assignee: Karlshamns AB, Karlshamns, Sweden

[21] Appl. No.: 466,124

[22] Filed: Jun. 6, 1995

Related U.S. Application Data

[62] Division of Ser. No. 289,535, Aug. 12, 1994, Pat. No. 5,474,835, which is a division of Ser. No. 975,335, Nov. 16, 1992, Pat. No. 5,352,817, which is a division of Ser. No. 546,372, Jun. 29, 1990, Pat. No. 5,164,522.

[51] Int. Cl.$^6$ ........................................ C07F 7/10
[52] U.S. Cl. .................... 556/423; 556/424; 556/425
[58] Field of Search .................... 556/423, 424, 556/425

[56] References Cited

U.S. PATENT DOCUMENTS

| | | | |
|---|---|---|---|
| 3,402,191 | 9/1968 | Morehouse | 556/423 |
| 3,471,541 | 10/1969 | Morehouse | 556/423 X |
| 3,565,936 | 2/1971 | Morehouse | 556/423 |
| 4,994,593 | 2/1991 | Lin et al. | 556/425 X |
| 5,164,522 | 11/1992 | McCarthy et al. | 556/424 X |
| 5,474,835 | 12/1995 | McCarthy et al. | 556/423 X |

*Primary Examiner*—Paul F. Shaver
*Attorney, Agent, or Firm*—Burns, Doane, Swecker & Mathis, L.L.P.

[57] ABSTRACT

A cationic silicone compound which can be employed in a variety of environments, such as a fiber lubricant, textile fabric softener, hair conditioner, and skin conditioner is formed from an aminosilicone compound which has the following Formula (I):

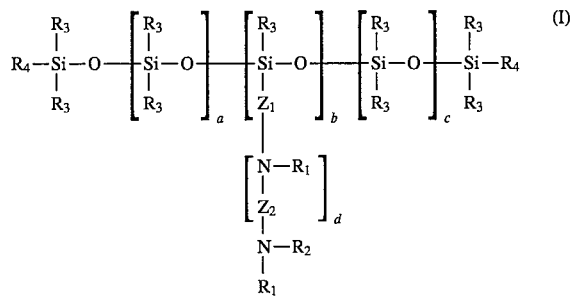

wherein a, b, and c are 0–300;

d is 0–4, preferably 1 or 2;

$R_1$ comprises hydrogen, an alkyl, aryl, alkynyl, alkenyl, alkyloxyalkylene group which may be unsubstituted or substituted with P, N, or S moieties;

$R_2$ is defined the same as $R_1$ and can also be a carboxylic acid residue preferably a fatty acid residues, with the proviso that where $R_2$ is a carboxylic acid residue, the $R_1$ attached to the terminal N is hydrogen;

$R_3$ is defined the same as $R_2$ and can also be alkoxy, aryloxy or oxyalkylene groups;

$R_4$ is defined the same as $R_3$ and can also be an amino-substituted alkyl group;

$Z_1$ and $Z_2$ can be the same or different and comprise an alkyl, aryl, alkenyl or alkynyl group with the proviso that if b is 0, then at least one of the $R_4$ groups comprises an amino-substituted alkyl group.

In particular, the aminosilicone is quaternized using known quaternizing agents, e.g., alkylation reagents.

7 Claims, No Drawings

CATIONIC SILICONES

This application is a divisional of application Ser. No. 08/289,535, filed Aug. 12, 1994, now U.S. Pat. No. 5,474,835, which is a divisional of Ser. No. 07/975,335, filed Nov. 16, 1992, now U.S. Pat. No. 5,352,817, which is a divisional of Ser. No. 07/546,372, filed Jun. 29, 1990, now U.S. Pat. No. 5,164,522.

BACKGROUND OF THE INVENTION

The present invention relates to cationic silicone compounds.

The use of silicone compounds in the treatment of synthetic fibers is known in the art. See, for example, the discussion of epoxy silicones in U.S. Pat. No. 2,947,771 to Bailey et al. Such silicone compounds are effective in both providing increased lubricity of the fiber and improved softness for fabrics made from these fibers. However, these epoxy silicones suffer from the disadvantage that they only possess a limited durability when employed with synthetic fibers.

The art has also looked to certain aminosilicones in the treatment of fibers. Because these silicones possess no net charge, they cannot be effectively bonded to cellulosic or proteinaceous materials. In fact, when used in connection with conventional polyester fiber/cotton blends, the aminosilicones will bond only to the polyesters within the blends.

In an attempt to overcome these problems, it is known to use cationic compounds which are bonded to the cellulosic materials. See, for example, the discussion in "Household Fabric Softeners—The Chemistry and Characteristics of Cationic Softeners" by J. P. McCarthy et. al., in *Soap, Cosmetics, and Chemical Specialties*, January 1989, page 33–35.

However, these cationic compounds also suffer from disadvantages because they impart only a moderate level of softness to the fibers. In addition, multiple launderings tend to remove the treatment thereby diminishing even this moderate level of softness.

Moreover, certain cationic compounds such as certain specific cationic polyorganodisiloxanes (see, for example, U.S. Pat. No. 4,472,566 to Ziemilis et al) and quaternary nitrogen derivatives of organosiloxanes (such as those discussed within U.S. Pat. No. 4,185,087 to Morlino) are known in the art. For example, the following cationic silicones are disclosed in U.S. Pat. No. 4,472,566:

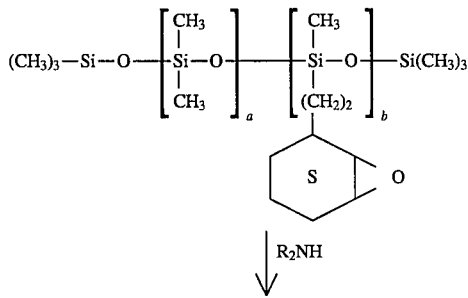

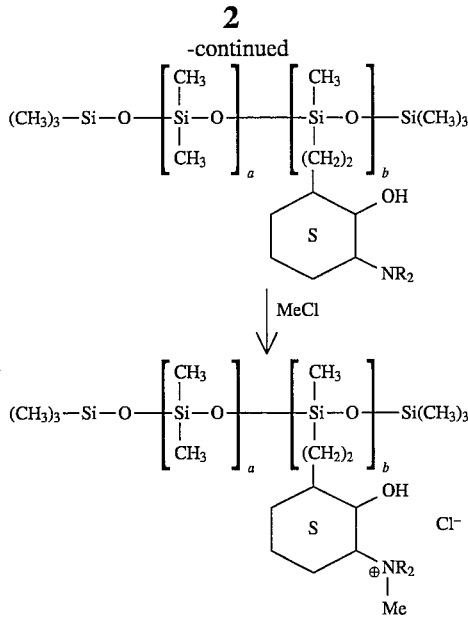

These compounds are traditionally employed in hair care products. In such compositions, the cationic compounds exhibit superior conditioning capability for hair because they have an affinity for bonding to proteinaceous substrates such as hair.

In addition, certain quaternary siloxane copolymers derived from siloxanes containing epoxy groups are disclosed in U.S. Pat. No. 4,895,964 to Margida, U.S. Pat. No. 4,891,166 to Schaefer et al, and Great Britain Patent 2,201,433A.

It is an object of the present invention to provide cationic silicone compounds which may be employed in a variety of environments such as a fiber lubricant, textile fabric softener, hair conditioner, and/or skin conditioner.

This and further objects will become apparent from the specification and claims that follow.

SUMMARY OF THE INVENTION

In accordance with the foregoing objectives, the present invention relates to a cationic silicone compound which can be employed in a variety of environments, such as a fiber lubricant, textile fabric softener, hair conditioner, and skin conditioner.

The cationic silicone according to the present invention is formed from an amino silicone compound which has the following Formula (I):

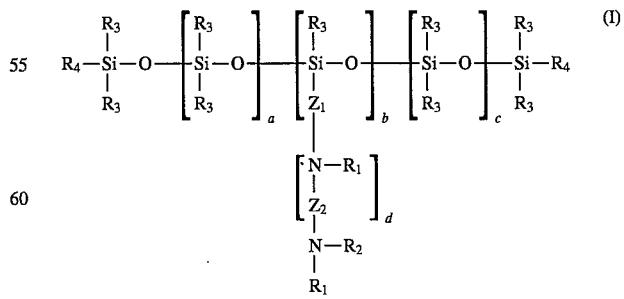

wherein a, b, and c are 0–300;

d is 0–4, preferably 1;

$R_1$ comprises hydrogen, or an alkyl, aryl, alkynyl, alkenyl, or oxyalkylene group which may be unsubstituted or substituted with P, N, or S moieties;

$R_2$ is defined the same as $R_1$ and can also be a carboxylic acid residue preferably a fatty acid residues, with the proviso that where $R_2$ is a carboxylic acid residue, the $R_1$ attached to the terminal N is hydrogen;

$R_3$ is defined the same as $R_2$ and can also be alkoxy, aryloxy or alkyloxyalkylene groups;

$R_4$ is defined the same as $R_3$ and can also be an amino-substituted alkyl group;

$Z_1$ and $Z_2$ can be the same or different and comprise an alkyl, aryl, alkenyl or alkynyl group with the proviso that if b is 0, then at least one of the $R_4$ groups comprises an amino-substituted alkyl group.

In particular, the aminosilicone is quaternized using known quaternizing agents, e.g., alkylation reagents.

The preferred cationic silicones according to the present invention include:

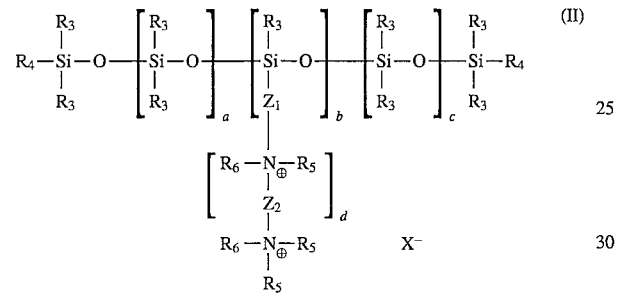
(II)

where $R_5$ is defined in the same manner a $R_1$ above, preferably, either a hydrogen or an oxyalkylene group;

$R_6$ is an unsubstituted or substituted alkyl or aryl group, preferably, an alkyl group;

$R_3$ and $R_4$ can be the same or different and comprises an alkyl group or an alkyloxyalkylene group;

$Z_1$ and $Z_2$ are the same or different and each represent an alkyl group;

b is 1–300;

d is 0–4, preferably 1; and

X is a counter ion, preferably, methosulfate.

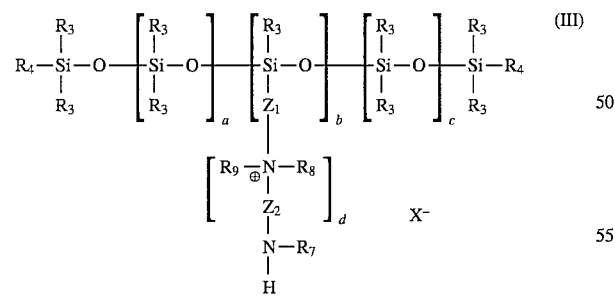
(III)

where $R_7$ is a carboxylic acid residue, preferably a fatty acid residue;

$R_8$ is defined in the same manner a $R_1$ above, preferably, either a hydrogen or an oxyalkylene group;

$R_9$ is an unsubstituted or substituted alkyl or aryl group, preferably, an alkyl group;

$R_3$ and $R_4$ can be the same or different and comprises an alkyl group or an alkyloxyalkylene group;

$Z_1$ and $Z_2$ are the same or different and each represent an alkyl group;

b is not less than 1;

d is 0–4, preferably 1; and

X is a counter ion, preferably, methosulfate.

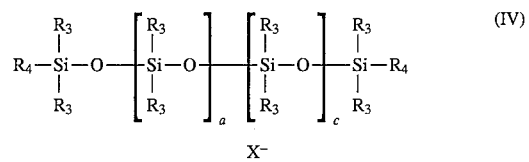
(IV)

where $R_3$ represents an alkyl group;

$R_4$ represents an amino substituted alkyl or aryl group, preferably, an amino substituted alkyl group comprising:

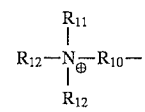

where $R_{10}$ is defined is the same manner as $R_1$ (except for hydrogen), preferably an alkyl group;

$R_{11}$ is an unsubstituted or substituted alkyl or aryl group, preferably, an alkyl group;

$R_{12}$ is either hydrogen or an oxyalkylene group; and

X is a counter ion, preferably, methosulfate.

The present invention also relates to certain novel compounds which are generally represented by formula (I) and the method for making these compounds. These compounds include:

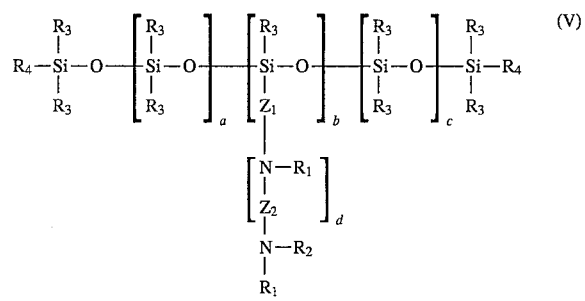
(V)

wherein b is 1–300;

d is 0–4, preferably 1;

$R_1$ and $R_2$ comprises an oxyalkylene group which may be unsubstituted or substituted with P, N, or S moieties, preferably unsubstituted;

$R_3$ and $R_4$ are the same or different and comprise an alkyl group or an alkyloxyalkylene group;

$Z_1$ and $Z_2$ can be the same or different and comprise an alkyl group.

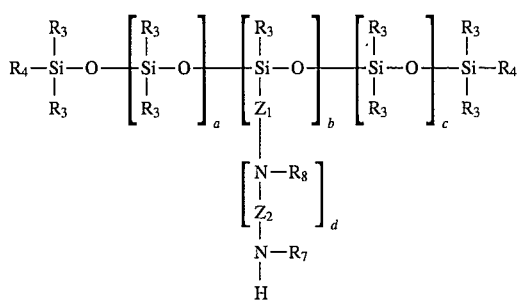 (VI)

wherein b is 1–300;

d is 0–4, preferably 1;

$R_7$ and $R_8$ are defined above;

$R_3$ and $R_4$ are the same or different and comprise an alkyl group or an alkyloxyalkylene group;

$Z_1$ and $Z_2$ can be the same or different and comprise an alkyl group.

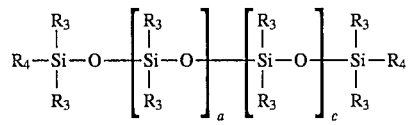 (VII)

where $R_4$ comprises certain amino substituted alkyl or aryl groups, preferably containing an amino substituted alkyl group;

$R_3$ is an alkyl group or an alkyloxyalkylene group.

In particular, $R_4$ comprises an alkoxylated, preferably ethoxylated, amino substituted alkyl group comprising:

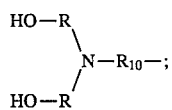

or an amidified amino substituted alkyl group comprising:

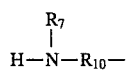

where $R_7$ and $R_{10}$ were defined above.

In still another aspect of the present invention, the cationic silicones are employed as lubricants for use with a variety of fibrous materials.

DETAILED DESCRIPTION OF THE PREFERRED EMBODIMENTS

The present invention relates to the reaction of an aminosilicone with a quarternizing agent in order to provide a cationic silicone compound.

The aminosilicones which can be employed in the formation of the cationic silicones of the present invention have the following formula (I):

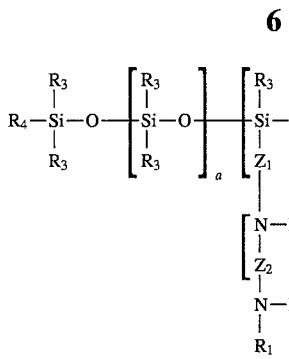 (I)

wherein a, b, and c are 0–300;

d is 0–4, preferably 1;

$R_1$ comprises hydrogen, an alkyl, aryl, alkynyl, alkenyl, oxyalkylene group which may be unsubstituted or substituted with P, N, or S moieties;

$R_2$ is defined the same as $R_1$ and can also be a carboxylic acid residue, preferably a fatty acid residue, with the proviso that where $R_2$ comprises a carboxylic acid residue, $R_1$ attached to the terminal N is hydrogen;

$R_3$ is defined the same as $R_2$ and can also be alkoxy, aryloxy or alkyloxyalkylene groups;

$R_4$ is defined the same as $R_3$ and can also be an amino-substituted alkyl group;

$Z_1$ and $Z_2$ can be the same or different and comprise an alkyl, aryl, alkenyl or alkynyl group;

with the proviso that if b is 0, then at least one of the $R_4$ groups comprises an amino-substituted alkyl group.

According to the process of the present invention, the compounds according to formula (I) are reacted with a quaternizing agent in order to form the cationic silicone.

The quaternizing agents which can be employed in the present invention include those known alkylation reagents such as alkyl sulfates, aryl sulfates, alkyl halides and aryl halides. Specific examples of these compounds include diethyl sulfate, dimethyl sulfate, methyl chloride, methyl iodide, benzyl iodide, and benzyl chloride.

Although the quaternizing agent will vary depending on the specific application, dimethyl sulfate is generally preferred.

A solvent can be employed to control the viscosity of the material during the reaction. Suitable solvents include isopropyl alcohol, ethyl alcohol, ethylene glycol, diethyl glycol, and polyoxyalkylenes. Isopropyl alcohol is preferred in applications where the odor of isopropyl alcohol is not critical or where flammability is not an important consideration.

In an example of the present invention, an aminosilicone according to formula (Ia) where at least one $R_1$ group is hydrogen is reacted with a quaternizing agent to form an amine salt according to formula (IIa). An example of the process according to the present invention is illustrated below:

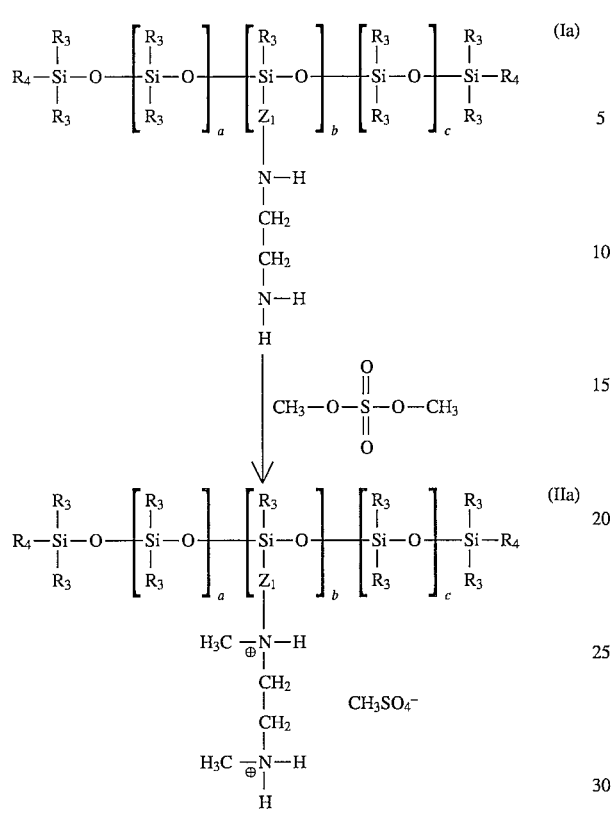

Although these reactions can be conducted at temperatures in the range of about 20° C. to about 160° C., the preferred temperature range is about 25° C. to about 40° C. The use of higher temperatures may introduce problems associated with discoloration.

Generally, these reactions are conducted under an inert atmosphere such as nitrogen to prevent discoloration, although they may be conducted in air.

In addition, the present invention also relates to certain novel aminosilicone compounds which are also generally represented by Formula (I) and methods for making these novel compounds. For example, certain aminosilicones employed in the process of the present invention can be alkoxylated and/or amidified prior to being reacted with the quaternizing agent.

The novel aminosilicones can be produced through the use of known aminosilicone compounds. Examples of known aminosilicone compounds which can be employed in producing these novel aminosilicones include aminopolysiloxane compounds such as Shin-Etsu KF-383, and Magnasoft fluid (Magnasoft is a trademark of Union Carbide). Such compounds are also generally represented by Formula (Ia) where $R_1$ and $R_2$ each represent hydrogen, and $R_3$ and $R_4$ each represent alkyl groups, preferably methyl groups.

Moreover, although the present invention will be described in terms of certain preferred embodiments, in particular, where d is 1 and $Z_2$ is —$CH_2CH_2$—, one of ordinary skill clearly would recognize that these discussions are equally applicable to all embodiments of the invention.

For example, the above discussed aminosilicone compound, i.e., an aminosilicone where at least one $R_1$ or $R_2$ is hydrogen, can be reacted with an alkylene oxide to convert the primary and secondary amine sites to tertiary amine sites. This reaction product, Figure (Va), in which none of the $R_1$ groups are hydrogen, can then be reacted with the quaternizing agent in order to form a quaternary amino compound.

The first step of this process provides an compound according to a formula (Va) where each of the $R_1$ and $R_2$ which were hydrogen have been replaced with an oxyalkylene group.

An example of the reaction is illustrated below:

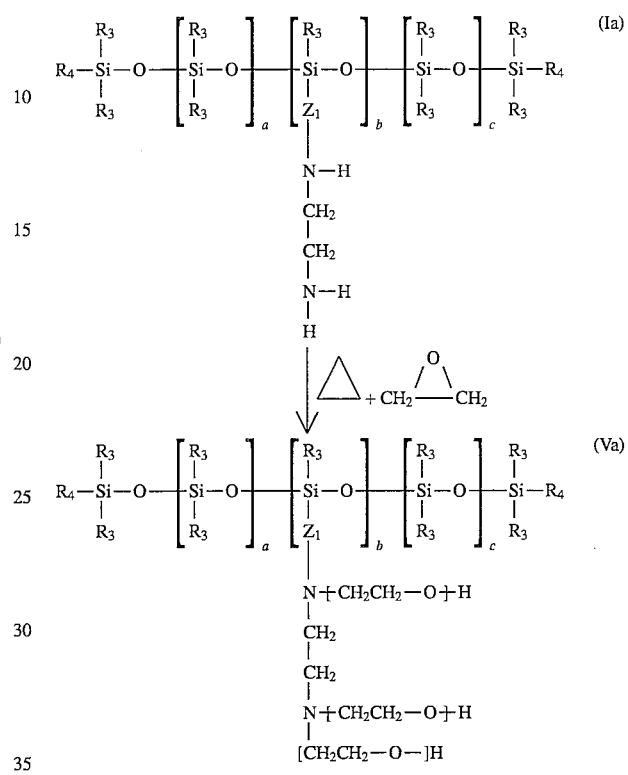

The alkylene oxides which can be employed include ethylene oxide, propylene oxide, butylene oxide, or mixtures thereof.

Preferably, alkoxylation is conducted at about 120° C. to about 160° C. in an oxygen-free atmosphere. Oxygen should be carefully excluded to prevent discoloration. Optionally, a solvent such as 2-propanol, may be used to facilitate reaction at temperatures of about 20° C. to about 110° C.

These alkoxylated tertiary nitrogen sites can then be reacted with the above described quaternizing agents so as to form the cationic, quaternary amine salts in the manner illustrated below. This compound is illustrated by formula (IIb):

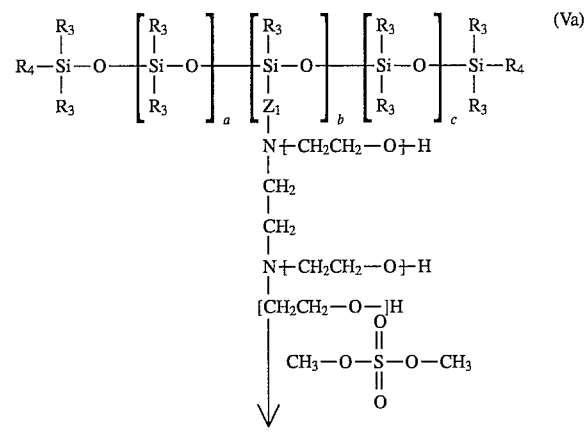

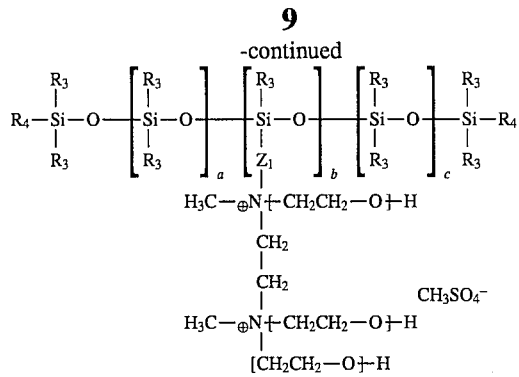

(IIb)

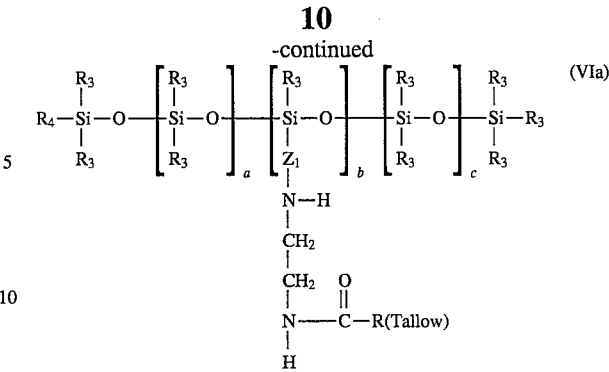

(VIa)

The preferred reaction conditions for this reaction are the same as those for the quaternization reaction previously described.

These quaternary amine salts can be either water insoluble or water soluble depending on the concentration of amino-containing mer found in the original aminosilicone.

In another embodiment of this invention, an additional novel family of aminosilicone compositions, also generally represented by Formula (I), may be made through an amidification process in order to introduce a carboxylic acid residue, preferably a fatty acid residue, onto the terminal N.

In a preferred embodiment, these compounds may be synthesized by reacting those aminosilicones described above with a glyceride in order to convert the amine into an amide. In order to perform this process, an aminosilicone must be selected such that both of the $R_1$ and the $R_2$ groups in the terminal N are hydrogen. It is apparent that the reaction product, as illustrated by Figure (VIa), comprises Figure (I) where $R_2$ comprises a substituted carboxy group.

In this process, any glyceride can be employed. Although oils such as coconut, palm, palm kernel, tallow, soybean, orange roughy, and jojoba are preferable.

An example of this reaction is illustrated below:

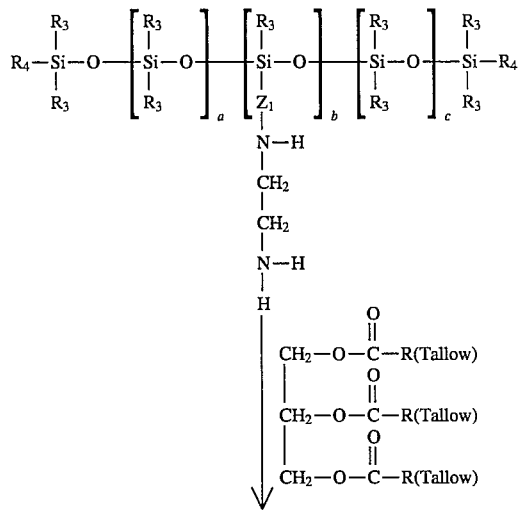

(Ia)

Preferably, these compositions are synthesized under the conditions subsequently described. Amidification of the primary amine site is conducted at about 120° C. to about 160° C. under an inert gas atmosphere to prevent discoloration.

The compositions resulting from amidification may be subsequently alkoxylated with alkylene oxide compositions as previously described. The entirely new family of compositions which result from this reaction, Figure (VIb), is also included within Formula (I) where each of the $R_1$ which were hydrogen, except for that $R_1$ group on the terminal N, have been replaced with oxyalkylene groups.

An example of this reaction is as follows:

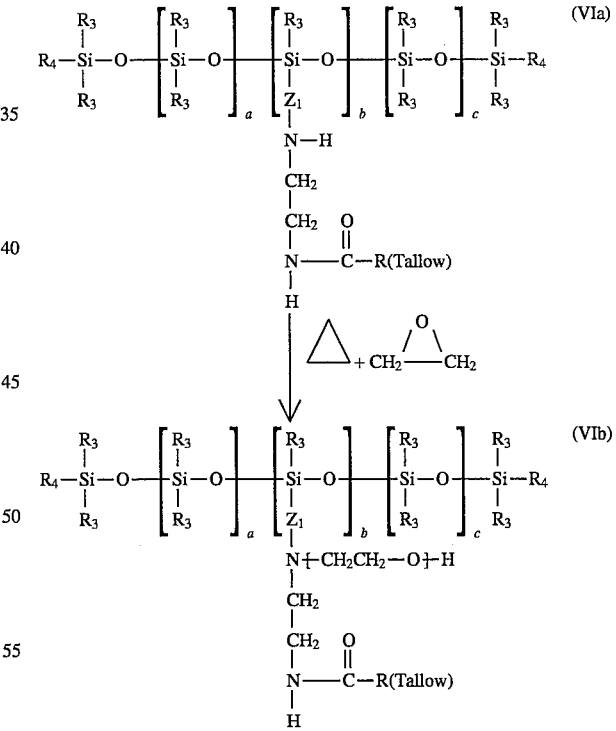

The resulting compositions may be quaternized by reaction with alkylating agents as previously described. The compositions which result from this reaction are illustrated by formula (IIIa).

An example of this process is illustrated below:

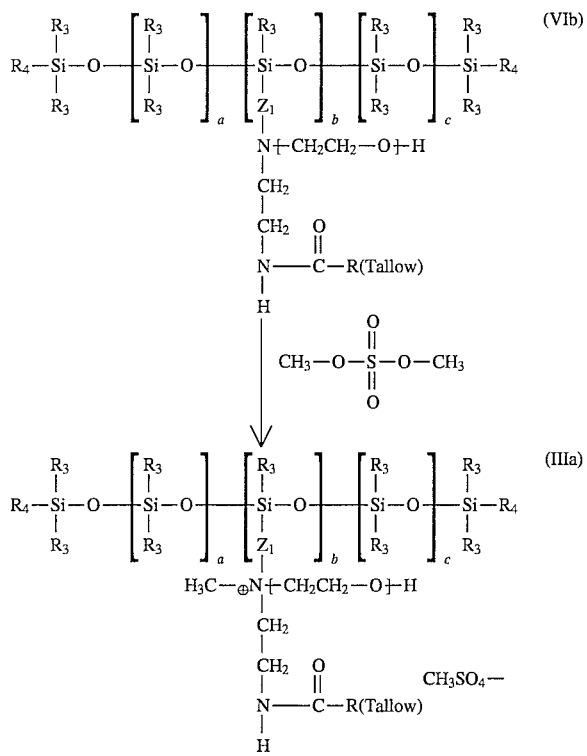

The amidified product, i.e., where $R_2$ is a fatty acid residue, may be alkylated directly after amidification, i.e., where no intermediate alkoxylation occurs.

The product, Formula (IIIb), resulting from this process is illustrated below.

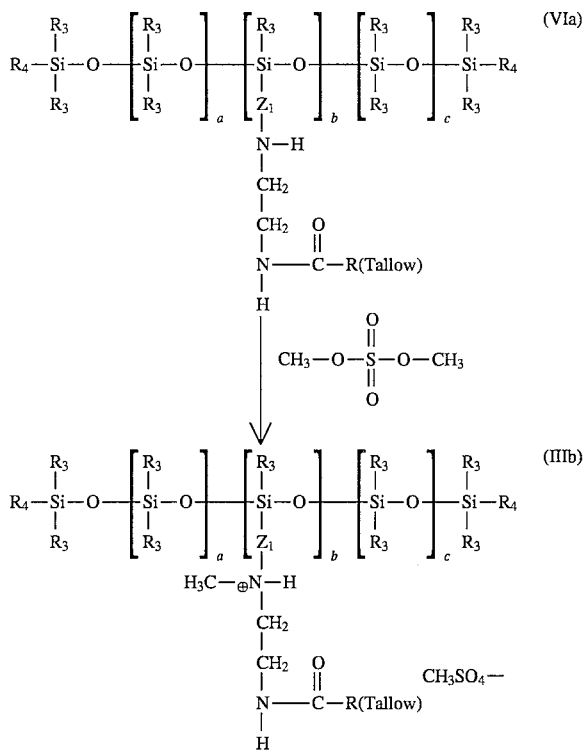

In yet another embodiment of the invention, the compound according to formula (I) where at least one of the $R_4$ groups is a substituted amino group, Formula (IVa), is employed in the quaternization process. Such compounds where the amino group is substituted with, e.g., hydrogen are known in the art.

In a preferred embodiment, b is equal to 0 while $R_4$ preferably comprises an amino substituted alkyl or aryl, more preferably, an amino substituted alkyl group. These compounds can be employed in the same manner as the previously discussed compounds.

For example, an amino salt, Formula (IVa), may be formed by the following process.

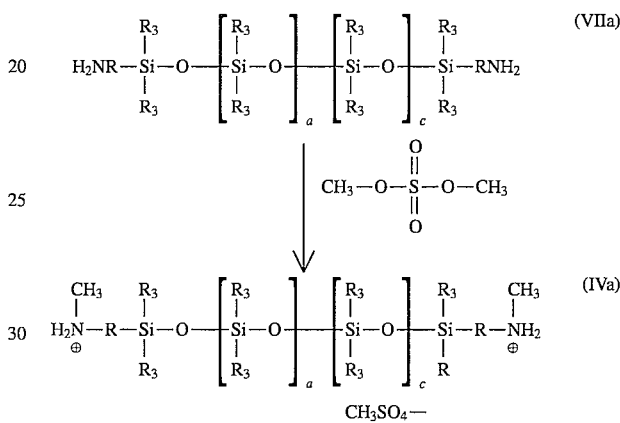

As was the case previously, these compounds may also be alkoxylated prior to quaternization. The resulting product is a novel class of aminosilicone compounds. For example, the compound of Formula (VIIa) may be reacted with ethylene oxide to form the following formula (VIIb):

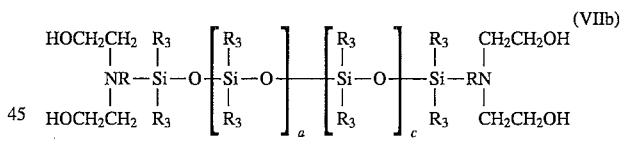

This compound may then be quaternized to form the following formula (IVb):

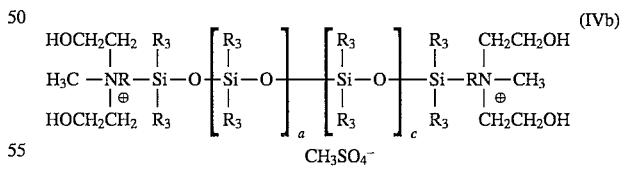

Furthermore, these compounds may also be amidified. For example, the compound according to formula (VIIa) may be reacted with a glyceride, such as tallow oil, to form a compound according to formula (VIIc) This also results in a novel class of aminosilicone compounds:

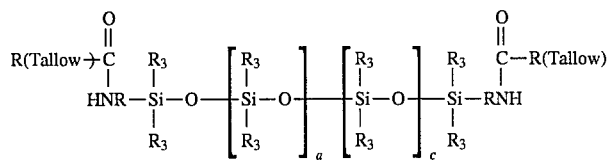

However, if the $R_4$ groups are amidified in the above manner, then the N in the $R_4$ group may not be reacted any further, i.e., they may not be alkoxylated or quaternized.

The cationic silicone compositions of the present invention can be employed as a lubricant for fibers such as polyester, nylon, acrylic, aramides, cotton, wool, and blends thereof.

Methods of application for these cationic silicones include those traditionally employed in the art, such as padding and by kiss roll. These materials can also be employed as treatments for hair, skin and textiles.

It is believed that the wide utility of these compositions is related to their ability to impart good boundary lubricity to a variety of substrates. On fiber and textiles, low boundary friction is perceived as softness. Similarly, on hair or skin, lower boundary friction imparts an aesthetic of softness or silkiness.

For use on textiles, a solution or dispersion of silicone is prepared and applied to a swatch of textile by padding. If necessary, auxiliary emulsifiers may be used to facilitate emulsification of the silicone. Following padding, the experimental fabric sample is dried in an oven at 100° C.–170° C. for a period of 3 minutes–20 minutes. Alternatively, the silicone may be dissolved in a solvent such as toluene or isopropyl alcohol.

These solvents are intended to be considered as examples. Other useful solvents will be apparent to those skilled in the art. After removal of the solvent, the fabric is cured in the aforementioned manner.

Application to synthetic fiber such as polyester may be achieved by applying an emulsion of said silicone to the polyester tow either before crimping a stuffer box or prior to passage through a relaxer oven. Following treatment and curing, the resulting product may be used in the original tow form or chopped into staple. One potential use for these products is as a fiberfill, which is used as filling materials in pillows, comforters, insulated clothing, and sleeping bags.

In another embodiment, fabrics may be treated by the silicone which has been dissolved in an organic solvent, e.g., dry cleaning fluid. The composition may also be used to condition fabrics, particularly during or immediately following a laundering process. The composition may be included in a laundering composition, in a composition intended to be added to the rinse subsequent to washing the fabrics, or included in a composition intended to be added with wet fabrics to a dryer.

For example, the cationic silicones may be added to a liquid or solid fabric washing product which, in addition to the cationic silicone may comprise surfactants selected from anionic, nonionic, and cationic surfactant materials, mixtures thereof, or with other surfactant materials, detergency builder materials such as water-soluble precipitating or sequestering builder material or ion-exchange builder materials, bleaches, such a peroxy bleaches, optionally together with bleach activators, alkaline materials such as sodium silicate, fillers such as sodium sulfate, and also other conventional ingredients of such compositions.

Alternatively, the cationic silicones may be employed within a rinse conditioning composition, for example, a liquid rinse conditioning composition which in addition to the cationic silicone may comprise electrolytes, emulsifiers, viscosity modifying agents, thickeners, colorants, and also other conventional ingredients of such compositions.

Still further, the cationic silicones may be employed in a product for use in a dryer, e.g., a hot air rotary dryer, for example, in the form of a powder contained within a dispensing device or in the form of a coating on, or impregnation of, a flexible substrate material, which may be in any suitable form, e.g., sheet form.

These cationic silicones may also be applied to hair by incorporation into formulated products such as conditioners, shampoos, and other hair care products.

Similar compositions and application techniques may be used with pelts of natural animal furs such as mink otter, raccoon and the like. Animal fur is also meant to include the coats of animals such as dogs and cats. These compositions may also be advantageously applied to synthetic furs made of acrylic and other fibers.

Application to skin may be achieved by formulating with emollients to make lotions, creams, and sunscreening preparations and applying to skin by rubbing, spraying and other techniques.

These cationic silicones can also be employed within automobile care products when formulated with appropriate cleansers, waxes, and solvents. These products may be in the form of pastes, creams, or liquids. They may be used for the care of exterior finishes and trim as well as for interior care of vinyl and plastics.

The cationic silicones according to the present invention may be also used in the treatment of glass, ceramic or mineral fibers. In such environments it can be effectively employed as an alternative to traditional silane coupling agents.

In order to further illustrate the present invention and the advantages associated therewith, the following specific examples, it being understood that the same are intended only as illustrative and in nowise limitive.

EXAMPLES

EXAMPLE 1

Preparation of Ethoxylated Aminopolysiloxane

A pressure reaction apparatus equipped with mechanical stirrer was charged with 900 g of Shin-etsu KF-393. 173 g of ethylene oxide was added at 120° C.–140° C. and stirred under a nitrogen atmosphere until the pressure and temperature indicated that all of the ethylene oxide had reacted. Analysis of weight percent tertiary amine content revealed 100% conversion.

EXAMPLE 2

Preparation of Ethoxylated Aminopolysiloxane Compositions

A pressure reaction apparatus equipped with a mechanical stirrer was charged with 888 g of Dow-Corning Softener SSF. 33 g of ethylene oxide was added at 120° C.–140° C. and stirred under a nitrogen atmosphere until pressure and temperature indicated that all of the ethylene oxide had reacted. Analysis of weight percent tertiary amine revealed 100% conversion. The product had an APHA color of less than 100.

EXAMPLE 3

Preparation of Ethoxylated Aminopolysiloxane Compositions

A pressure reaction apparatus equipped with a mechanical stirrer was charged with 4156 g of Shin-Etsu KF-393. 780 g of ethylene oxide was added at 120° C.–140° C. and stirred under a nitrogen atmosphere until pressure and temperature indicated that all ethylene oxide had reacted. Analysis of weight percent tertiary amine content revealed 100% conversion. The product color was less than 100 APHA.

The ethoxylated aminopolysiloxane was cooled to 27° C. and 1580 g removed. To the remaining 3280 g was added 750 g of isopropanol and 292 g of dimethyl sulfate. After thorough mixing, 1951 g of this material was removed. This product had a free amine content of 48%. The product's color was less than 100 APHA.

Using good stirring, 165 g of isopropanol and 246 g of dimethyl sulfate was added to the remaining 2370 g of ethoxylated aminopolysiloxane. The product contained 11.4% free amine, 75.5% solids and APHA color of less than 100.

EXAMPLE 4

Preparation of Ethoxylated Aminopolysiloxane Quaternary Compositions.

A 1500 ml. beaker was charged with 900 g of ethoxylated Shin-Etsu KF859. Then, 14.52 g of dimethyl sulfate was added at 27° C. using mechanical agitation. The resulting product had a free amine content of 8.8% and APHA color of less than 150.

EXAMPLE 5

Preparation of ethoxylated aminopolysiloxane quaternary compositions

A 1500 ml. beaker was charged with 739 g of ethoxylated Magnasoft Fluid. Then, 25 g of isopropanol and 17.86 of diethyl sulfate were added with mechanical agitation and maintained at 55° C.–65° C. The resulting product had a free amine content of 29%.

EXAMPLE 6

Preparation of Aminopolysiloxane Quaternary Salt Compositions

In a 1500 ml beaker, 1000 g of Magnasoft Fluid and 100 bg of isopropanol were thoroughly mixed using mechanical agitation. After heating to 71° C., 13 g of dimethyl sulfate was added while maintaining good agitation. The final product had a free amine content of 36% and solids of 92 weight percent.

EXAMPLE 7

Preparation of Ethoxylated Amide Aminopolysiloxane Quaternary Compounds

A pressure reaction vessel equipped with a mechanical stirrer was charged with 2770 g of Shin-Etsu KF-393 and 1090 g of tallow. While stirring, the mixture was heated for 6 hours at 160° C. under a nitrogen atmosphere.

The amide aminopolysiloxane intermediate was then cooled to 104° C. Ethylene oxide was added until 100% tertiary amine was achieved. A total of 308 g of ethylene oxide was required for complete conversion to tertiary amine.

Ethoxylated amide aminopolysiloxane from the preceding step was quaternized by the following procedure. Using good agitation, 3872 g of ethoxylated amide aminopolysiloxane and 360 g of isopropanol were brought to a temperature of 27° C. Then, while maintaining good agitation, 412 g of dimethyl sulfate was added. Following addition of dimethyl sulfate, an additional 320 g of isopropanol were added. The final product contained 12.6% free amine and had a color of 2 on a Gardner (1933) scale. The actives content of the final product was 80 weight percent.

While this invention has been described in terms of various preferred embodiments, the skilled artisan will appreciate that various modifications, substitutes, omissions, and changes may be made without the departing from the spirit thereof. Accordingly, it is intended that the scope of the present invention be limited solely by the scope of the following claims including equivalents thereof.

We claim:

1. A cationic silicone comprising at least one

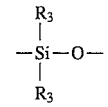

structural unit and at least one structural unit having the formula:

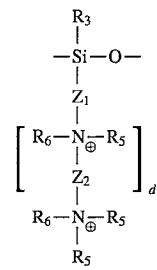

where d is 0–4;

$R_3$ is an alkyl group, aryl group, alkynyl group, alkenyl group, or an alkyloxyalkylene group;

$Z_1$ and $Z_2$ are the same or different and are each an alkyl group;

$R_5$ is the same or different and is a hydrogen, alkyl, aryl, alkynyl, alkenyl or oxyalkylene group; and $R_6$ is the same or different and is an alkyl or aryl group.

2. The cationic silicone of claim 1 where $R_3$ is an allyl group or an alkyloxyalkylene group.

3. The cationic silicone of claim 1 where $R_5$ is hydrogen or an oxyalkylene group.

4. The cationic silicone of claim 1 where at least one $R_6$ is an alkyl group.

5. The cationic silicone of claim 1 where d is 1.

6. A cationic silicone comprising at least one

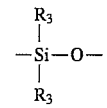

structural unit and end groups comprising:

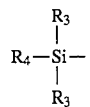

where $R_3$ can be the same or different and is an alkyl group, aryl group, alkynyl group, alkenyl group, or alkyloxyalkylene group; and $R_4$ has the following formula:

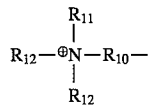

where $R_{10}$ is an alkyl group, aryl group, alkynyl group, alkenyl group or alkyloxyalkylene group; $R_{11}$ is an alkyl or aryl group and $R_{12}$ is hydrogen or an oxyalkylene group.

7. The cationic silicone according to claim 6 where $R_3$ is an alkyl group or an alkyloxyalkylene group, and $R_{10}$ and $R_{11}$ are each an alkyl group.

* * * * *